United States Patent [19]

Loozen et al.

[11] Patent Number: 4,634,694
[45] Date of Patent: Jan. 6, 1987

[54] NOVEL Δ4- AND Δ5-ANDROSTENE DERIVATIVES AND PHARMACEUTICAL COMPOSITIONS CONTAINING THESE DERIVATIVES

[75] Inventors: Hubert J. J. Loozen, Uden; Pieter J. N. van Luit, Ja Oss, both of Netherlands

[73] Assignee: Akzo N.V., Arnhem, Netherlands

[21] Appl. No.: 688,368

[22] Filed: Jan. 2, 1985

[30] Foreign Application Priority Data

Jan. 14, 1984 [NL] Netherlands ................. 8400126

[51] Int. Cl.$^4$ ............................................. A61K 31/56
[52] U.S. Cl. ....................................... 514/177; 514/178; 514/182; 260/397.3; 260/397.4; 260/397.5
[58] Field of Search .............. 260/397.3, 397.4, 397.5; 514/178, 177, 182

[56] References Cited

U.S. PATENT DOCUMENTS 4,289,762  9/1981  Metcalf et al. ................ 424/242
4,322,416  3/1982  Metcalf et al. ................ 424/242
4,473,564  9/1984  De Winter et al. ............ 260/397.4

FOREIGN PATENT DOCUMENTS 100566  2/1984  European Pat. Off. ......... 424/242

OTHER PUBLICATIONS

Chemical Abstracts, vol. 96, 96:116466t, 1982.

Primary Examiner—Elbert L. Roberts

[57] ABSTRACT

The invention relates to novel steroids having the formula:

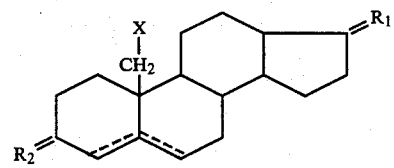

wherein
X=CH$_2$—S—R$_3$ or S—S—R$_4$;
R$_1$=O or H (βR$_5$);
R$_2$=O or H (βR$_6$);
R$_3$=H, acyl (1–18C) or alkyl (1–4C);
R$_4$=H, acyl (1–18C) or hydrocarbyl (1–18C), the acyl or hydrocarbyl group being optionally substituted;
R$_5$=OH, O acyl (1–18C) or an ether group;
R$_6$=OH, O acyl (1–18C) or an ether group;

and the dotted lines represent a carbon-carbon bond in 4,5- or 5,6 position; to processes for their preparation and to pharmaceutical compositions containing these steroids as active constituents.

The novel compounds possess particularly aromatase-inhibiting properties.

8 Claims, No Drawings

NOVEL Δ⁴- AND Δ⁵-ANDROSTENE DERIVATIVES AND PHARMACEUTICAL COMPOSITIONS CONTAINING THESE DERIVATIVES

The invention relates to novel 3-oxo-$\Delta^4$- and 3$\beta$-hydroxy-$\Delta^4$-androstene derivatives and the $\Delta^5$-analogs thereof which are characterised by the presence of a sulphur-containing substituent in position 19. The invention also relates to processes for the preparation of such compounds and to pharmaceutical compositions containing these steroids, and to the use of these compounds as inhibitors of the biosynthesis of steroids. particularly as aromatase inhibitors.

By aromatase inhibitors there are understood substances which are capable of inhibiting the enzyme or the enzyme complex, referred to by the name aromatase, in its action of converting a steroidal 3-oxo-$\Delta^4$-10-methyl system to an aromatic (phenolic) ring-A system.

The "aromatisation" of androgens to oestrogens is an important physiological reaction in the body and normally takes place as needed. There are, however, clinical indications of excessive production of oestrogens (hyperoestrogenicity). By administration of aromatase-inhibiting substances, such as the novel compounds according to the invention, the production of oestrogens can be brought back to the desired level. For example, in women in the peri-menopause with excessive oestrogen production, the risk of breast cancer and/or cancer of the uterus can be reduced with aromatase inhibitors. Aromatase inhibitors can also offer relief in the case of anovulation in hyperoestrogenicity as a consequence of obesity. In men, aromatase inhibitors can for example have an advantageous effect in the case of gynaecomastia in adolescents or in the case of prostate hypertrophy.

Various substances have already been proposed as aromatase inhibitors, for exemple: testolactone (U.S. Pat. No. 2,744,120), 4-hydroxy-$\Delta^4$-androstene-3,17-dione and esters thereof (see. for example, U.S. Pat. No. 4,235,893), 10-(1,2-propadienyl)-$\Delta^4$-oestrene-3,17-dione (U.S. Pat. No. 4,289,762) and 10-(2-propynyl)-$\Delta^4$-oestrene-3,17-dione (J.A.C.S. 1981, 103 3221 and U.S. Pat. No. 4,322,416).

The present invention relates to a novel group of $\Delta^4$- and $\Delta^5$- androstene derivatives having the general formula:

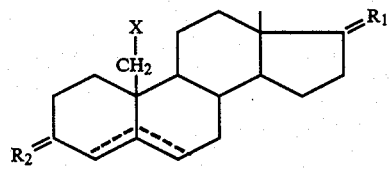

wherein
X=CH₂—S—R₃ or S—S—R₄;
R₁=O or H($\beta$R₅);
R₂=O or H($\beta$R₆);
R₃=H, acyl(1–18C); or alkyl(1–4C);
R₄=H, acyl(1–18C) or hydrocarbyl(1–18C) the acyl or hydrocarbyl group being optionally substituted;
R₅=OH, Oacyl(1–18C) or an ether group;
R₆=OH, Oacyl(1–18C) or an ether group;
and the dotted lines represent a carbon-carbon bond in 4,5- or 5,6-position.

R₁ is preferably O.

R₂ is preferably O, H($\beta$OH) or H($\beta$Oacyl(1–18C).

R₄ is preferably acyl (1–18C) or alkyl (1–18C), with the proviso that these groups can optionally be substituted by hydroxy, oxo, alkoxy, mercapto, alkylthio, amino, substituted amino, carboxyl and/or ester groups. If R₅ is present, then it is preferably OH or Oacyl(1–18C).

The acyl group optionally present in R₂ to R₆ inclusive is, as the suffix (1–18C) already indicates, derived from an organic carboxylic acid having 1–18 carbon atoms. As examples thereof there may be mentioned formic acid, acetic acid, propionic acid, butyric acid, isobutyric acid, trimethylacetic acid, valeric acid, capric acid, pelargonic acid, lauric acid, palmitic acid, phenylacetic acid, phenylpropionic acid, cyclopentylpropionic acid, cyclohexylcarboxylic acid, cyclooctylacetic acid, benzoic acid, fumaric acid, maleic acid and succinic acid.

If R₄ is an acyl group, this group can not only be derived from one of the abovementioned organic carboxylic acids but also from a substituted variant of these carboxylic acids, for example aminoacids or hydroxy carboxylic acids, such as alanine, lysine, threonine, lactic acid, citric acid; and the like.

The ether group optionally present in R₅ and/or R₆ is, for example, a hydrocarbon ether group, such as the methyl ether, ethyl ether, butyl ether, cyclopentyl ether or cyclohexenyl ether group and the like, an aromatic ether group, such as the benzyl ether group, or a heterocyclic ether group, such as, for example, the tetrahydropyranyl ether group.

By the alkyl group optionally present in R₃ there is meant methyl, ethyl, propyl, isopropyl, butyl, isobutyl or t.-butyl.

The alkyl group optionally present in R₄ can, in addition to one of the alkyl groups mentioned above for R₃, be a higher homologue (up to and including 18C atoms) thereof or a substituted variant of one of there alkyl(-1–18C) groups, for exemple 2-amino-3-hydroxy-3-oxo-propyl, 2-hydroxy-2-oxo-ethyl, 2-hydroxy-ethyl, 3-hydroxy-2-mercapto-propyl, and the like.

The invention thus relates to the novel androstene derivatives having the general formula I and also to these androstene derivatives for use as aromatase inhibitors, usually in the form of pharmaceutical compositions which contain said androstene derivatives as active ingredient.

The novel compounds can be administered in the conventional manner, enterally (orally or anally), parenterally (for example subcutaneously, intravenously or intramuscularly) or locally (via the skin or the mucous membranes, e.g. by inhalation), in combination with usual pharmaceutical auxiliaries, in the form of tablets, pills, dragees, lozenges, powders, capsules, microcapsules, aerosols, emulsions, suspensions, solutions, suppositories, ointments, creams or lotions. The pharmaceutical compositions can be prepared in accordance with known galenical methods.

The novel androstene derivatives can be prepared by methods which are in themselves obvious.

For the preparation of the androstene derivatives having a 19-(thio-methyl) group (X is CH₂SR₃), a corresponding 19-(hydroxymethyl) compound is converted to its sulphonate by reaction with an organic sulphonic acid halide, for example tosyl chloride or mesyl chloride, after which the sulphonate thus obtained is converted to the 19-(mercaptomethyl), 19-(alkylthiomethyl) or 19-(acylthiomethyl) compound in a similar manner to that described for corresponding 19-sulphonates in EP-A-0100566.

The 19-(hydroxymethyl)-steroid to be used as the starting material can conveniently be obtained by hydration of the corresponding 10-ethenyloestrene compound, which is described, for example, in J. Chem. Soc., Perkin Trans. I, 1977, No. 17, 1916–1924. This hydration can for example be carried out with the aid of boron compounds and hydrogen peroxide in accordance with a reaction referred to as "hydroboration". A suitable boron compound for this purpose is, for example, 9-borabicyclo[3.3.1.]nonane. An alkylated borane compound is first formed, and this is reacted with alkaline hydrogen peroxide to give a boric acid ester, which in turn is easily hydrolysed to the desired alcohol.

For the preparation of the 19-(alkyldithio) compounds (X=SSR) it is possible to start from, for example, the corresponding 19-mercapto compounds, which are also described in EP-A-0100566.

A general method for preparing the dithio compounds is the oxidative coupling of the 19-mercapto-steroid with a mercapto compound $R_4SH$, which method is known in peptide chemistry. The oxidation may be performed with molecular oxygen or with e.g. potassium ferricyanide.

A more convenient method, also starting in principle from the 19-mercapto-steroid and $R_4SH$, is to make one of the mercapto reactants reactive by reaction with a suitable activator and then reacting the activated mercapto compound with the other mercapto compound.

Thus, the 19-mercapto-androstene compounds are, for example, allowed to react with an S-alkyl-alkanethiosulphonate (obtained by oxidation of a diakyl disulphide with hydroqen peroxide) in a suitable solvent, for example tetrahydrofuran, in the presence of a base, for example sodium amide (see, for this type of reaction, Receuil 88 (1969), page 519, and, for the preparation of the reagent, also J. Org. Chem. 29, (1964), pages 1632–1635).

Reaction of the 19-mercapto steroid with S-methyl-methanethiosulphonate($R_4$=methyl) gives the 19-(methyldithio) compound; reaction with, for example, S-propyl-propanethiosulphonate ($R_4$=propyl) gives the 19-(propyldithio) compound, and so on.

In another method for the preparation of the dithio compounds the 19-mercapto steroid is reacted, in a basic medium, with reactive alkylated disulphides, for example alkylthio-dialkyl-sulphonium salts (Helv. Chim. Acta 59 (1976), pages 1307–1311). These reactive sulphonium salts, in particular sulphonium tetrafluoborates, are prepared from a symmetrical disulphide and a trialkyloxonium tetrafluoborate.

Examples of reactive alkylated disulphides in the form of sulphonium salts are: methylthiodimethylsulphonium tetrafluoborate, methylthiomethyl-ethylsulphonium tetrafluoborate, propylthiopropyl-ethyl-sulphonium tetrafluoborate, dodecylthio-dodecyl-ethylsulphonium tetrafluoborate, and so on. These then give steroids having a 19-methyldithio group, a 19-propyldithio group, a 19-dodecyldithio group and so on. By varying the alkyl group in the symmetrical disulphide from which the reactive sulphonium salt is prepared, the various 19-dithio steroids can be obtained.

Another convenient method consists of first activating the 19-mercapto steroid, e.g. by reacting it with methoxycarbonylsulphenyl chloride (SCM-Cl). The thus-obtained activated 19-mercapto steroid, carrying a

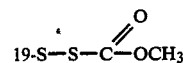

group is then reacted with the mercapto compound $R_4SH$.

SCM-Cl can also be used to activate the compound $R_4SH$, whereafter the activated $R_4S$-SCM compound is reacted with the 19-mercapto steroid.

Another mercapto-activating compound is, for example, t.butyl-azo-carboxylate

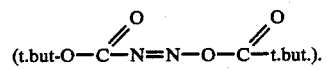

For the 19-acyldithio compounds, the "free" dithio compounds ($R_4$=H) can also first be prepared and these are then acylated in the conventional manner to give compounds wherein $R_4$=acyl (1–18C).

In all the reactions mentioned above, the hydroxyl or oxo groups present elsewhere in the steroid skeleton or in the substituent to be introduced are temporarily protected, if desired. An oxo group can be protected in the form of its acetal, for example the ethylenedioxy-acetal or the neopentylenedioxy-acetal. A hydroxyl group can be protected, where necessary, in the form of an ester, for example the acetate, or an ether, for example the tetrahydropyranyl ether. For end products having an ester or ether group in position 3 and/or 17 it is possible, where desired, to start, in the abovementioned reactions for the introduction of the 19-substituent, from a steroid compound having the desired ester or ether group already present in position 3 and/or 17.

After introduction of the 19-substituent X, the substituents desired in position 3 and/or 17 of the steroid skeleton can, if they are not yet present, still be introduced or produced by modification. For example, 3- or 17-hydroxyl group can be oxidised to the oxo group by the Oppenauer method or by the $CrO_3$ oxidation method. A 3- or 17-oxo group present can, if desired, be reduced to a hydroxyl group, for example with the aid of a complex metal hydride, such as sodium borohydride.

Ester and/or ether groups present in position 3 and/or 17 can, if desired, be hydrolysed to the hydroxyl group and a hydroxyl group can, if desired, be esterified or etherified in accordance with standard methods.

The invention is illustrated by the following examples.

EXAMPLE I (a)

3β-Hydroxy-19-(hydroxymethyl)-$\Delta^5$-androsten-17-one-17-ethylene-acetal

A solution of 0.34 g of 3β-hydroxy-10-ethenyl-$\Delta^5$-oestren-17-one-17-ethylene-acetal in 6.9 ml of tetrahydrofuran was added to 4.5 ml of an 0.5 molar solution of 9-borabicyclo[3.3.1.]nonane in tetrahydrofuran. The reaction mixture was heated under reflux for 4 hours. After it had cooled, the reaction mixture was placed in an ice bath, 0.6 ml of ethanol, 0.2 ml of 6N sodium hydroxide solution and 0.4 ml of 30% strength hydrogen peroxide solution were added and the mixture was stirred for 1 hour at room temperature.

The reaction mixture was poured out into water and extracted with methylene chloride. The extract was evaporated and the residue was purified by chromatography. Yield: 0.18 g of 3β-hydroxy-19-(hydroxymethyl)-Δ$^5$-androsten-17-one-17-ethylene-acetal.

(b)
3β-Hydroxy-19-(tosyloxymethyl)-Δ$^5$-androsten-17-one-17-ethylene-acetal 0.095 g of tosyl chloride was added to a solution of 0.18 g of 3β-hydroxy-19-(hydroxymethyl)-Δ$^5$-androsten-17-one-17-ethylene-acetal in 10 ml of dry pyridine. The reaction mixture was stirred for 15 hours at room temperature under a nitrogen atmosphere. It was then poured out into water and extracted with methylene chloride.

The extract was evaporated and the residue was purified by chromatography.

Yield: 0.11 g of 3β-hydroxy-19-(tosyloxymethyl)-Δ$^5$-androsten-17-one-17-ethylene-acetal.

(c)
3β-Hydroxy-19-(methylthiomethyl)-Δ$^5$-oestren-17-one-17-ethylene-acetal 0.05 g of CH$_3$SLi (obtained by reduction of dimethyl disulphide with lithium in liquid ammonia) was added to a solution of 0.11 g of 3β-hydroxy-19-(tosyloxymethyl)-Δ$^5$-androsten-17-one-17-ethylene-acetal in 5 ml of dimethylformamide under a nitrogen atmosphere. The mixture was stirred for 20 minutes at 70° C. and then poured out into ice water. After it had been stirred for 1 hour, the precipitate was removed by suction filtration. Yield: 0.07 g of 3β-hydroxy-19-(methylthiomethyl)-Δ$^5$-androsten-17-one-17-ethylene-acetal.

(d) 3β-Hydroxy-19-(methylthiomethyl)-Δ$^5$-androsten-17-one

A solution of 0.07 g of 3β-hydroxy-19-(methylthiomethyl)-Δ$^5$-androsten-17-one-17-ethylene-acetal in 5 ml of acetone, to which 0.6 ml of 2N hydrochloric acid had been added, was stirred for 16 hours at room temperature and then poured out into water, neutralised with NaHCO$_3$ and extracted with methylene chloride. The extract was evaporated and the residue was purified by crystallisation. Yield: 0.05 g of 3β-hydroxy-19-(methylthiomethyl)-Δ$^5$-androsten-17-one, melting point 100° C., $[α]_D^{20}= -36.6$ (in dioxane).

EXAMPLE II (a)
3β-Hydroxy-10-ethenyl-Δ$^5$-oestren-17-one-3-tetrahydropyranyl ether-17-ethylene-acetal 51 ml of dihydropyran and 340 mg of p-toluenesulphonic acid were added to a solution of 17 g of 3β-hydroxy-10-ethenyl-Δ$^5$-oestren-17-one-17-ethylene-acetal in 255 ml of dry tetrahydrofuran, with stirring and under a nitrogen atmosphere. The reaction mixture was stirred for 4 hours at room temperature and under nitrogen and was then poured out into water, to which some sodium bicarbonate had been added. Extraction with ether and evaporation of the extract gave 21 g of 3β-hydroxy-10-ethenyl-Δ$^5$-oestren-17-one-3-tetrahydropyranyl ether-17-ethylene-acetal, which was employed without further purification in the next reaction.

(b) 3β-Hydroxy-19-(hydroxymethyl)-Δ$^5$-androsten-17-one-3-tetrahydropyranyl ether-17-ethylene-acetal Following a similar procedure to that described in Example I(a), 21 g of the 10-ethenyl compound, obtained in Example II(a), were converted to 15.7 g of the title compound, melting point 170°-171° C.

(c) 3β-Hydroxy-19-(tosyloxymethyl)-Δ$^5$-androsten-17-one-3-tetrahydropyranyl ether-17-ethylene-acetal Following a similar procedure to that described in Example I(b), 5.0 g of the 19-(hydroxymethyl) compound, obtained in Example II(b), were converted to 6.5 g of the title compound, melting point 138° C.

(d)
3β-Hydroxy-19-(methylthiomethyl)-Δ$^5$-androsten-17-one-3-tetrahydropyranyl ether-17-ethylene acetal Following a similar procedure to that described in Example I (c), 3.0 g of the 19-(tosyloxymethyl) compound, obtained in Example II (c), were converted to 2.2. g of the title compound.

(e)
3β-Hydroxy-19-(methylthiomethyl)-Δ$^5$-androsten-17-one 2 g of 3β-hydroxy-19-(methylthiomethyl)-Δ$^5$-androstene-17-one-3-tetrahydropyranyl ether-17-ethylene-acetal were dissolved in 30 ml of acetone to which 0.3 ml of concentrated hydrochloric acid had been added. The reaction mixture was left to stand at room temperature for 16 hours. It was then poured out into water, neutralised with NaHCO$_3$ and extracted with methylene chloride. The extract was evaporated and the residue was purified by chromatography. Yield: 1.2 g of 3β-hydroxy-19-(methylthiomethyl)-Δ$^5$-androsten-17-one, melting point 100° C., $[α]_D^{20}= -36.6$ (in dioxane).

EXAMPLE III 19-(Methylthiomethyl)-Δ$^4$-androstene-3,17-dione 6 ml of cyclohexanone and a solution of 1.2 g of aluminium isopropoxide in 4 ml of dry toluene were introduced into a solution of 1 g of 3β-hydroxy-10-(methylthiomethyl)-Δ$^5$-androsten-17-one in 40 ml of dry toluene. The mixture was boiled for 1 hour under reflux, in a nitrogen atmosphere. After 6.4 g of sodium potassium tartrate had been added, the reaction mixture was poured out into water and extracted with methylene chloride. After evaporation of the extract, the residue obtained was purified by chromatography over silica gel, and crystallation. Yield: 0.8 g of 19-(methylthiomethyl)-Δ$^4$-androstene-3,17-dione, melting point 92° C., $[α]_D^{20}= +163.2$ (in dioxane).

EXAMPLE IV (a)
3β-Hydroxy-19-(tosyloxymethyl)-Δ$^5$-androsten-17-one

Following a similar procedure to that described in Example I (d), 1 g of 3β-hydroxy-19-(tosyloxymethyl)-Δ$^5$-androsten-17-one-17-ethylene-acetal was converted to 0.8 g of the title compound.

(b)
3β-Hydroxy-19-(mercaptomethyl)-Δ$^5$-androsten-17-one

A solution of 0.8 g of 3β-hydroxy-19-tosyloxymethyl-Δ$^5$-androsten-17-one and 0.4 g of NaSH.H$_2$O in 16 ml of dimethylformamide was heated to 80° C. for 75 minutes, with stirring. After the reaction mixture had cooled, it was poured out into ice water and extracted with ether/tetrahydrofuran. The extract was evaporated and the residue was purified by chromatography over silica and crystallisation from methylene chloride- /acetone. Yield: 0.2 g of 3β-hydroxy-19-(mercaptomethyl)-Δ$^5$-androsten-17-one.

EXAMPLE V

19-Mercaptomethyl)-Δ$^4$-androstene-3,17-dione

Following a similar procedure to that described in Example III, 0.2 g of 3β-hydroxy-19-(mercaptomethyl)-Δ$^5$-androsten-17-one was oxidised to 0.15 g of the title compound.

EXAMPLE VI

3β-Hydroxy-19-heptanoylthiomethyl-Δ$^5$-androsten-17-one-3-heptanoate 1.5 ml of heptanoyl chloride were added, with stirring, to a cooled solution of 1 g of 3β-hydroxy-19-(mercaptomethyl)-Δ$^5$-androsten-17-one in 10 ml of dry pyridine. The reaction mixture was stirred for 2 hours at room temperature. Conventional working-up and purification gave 1.1 g of 3β-hydroxy-19-heptanoylthiomethyl-Δ$^5$-androsten-17-one-3-heptanoate.

EXAMPLE VII

3β-Hydroxy-19-methylthiomethyl-Δ$^5$-androsten-17-one-3-undecanoate and 3-heotanoate 0.8 ml of undecanoyl chloride was added to a solution of 1 g of 3β-hydroxy-19-methylthiomethyl-Δ$^5$-androsten-17-one in 10 ml of dry pyridine. The reaction mixture was stirred for 1 hour at room temperature. Conventional working-up and purification gave 0.9 g of 3β-hydroxy-19-methylthiomethyl-Δ$^5$-androsten-17-one-3-undecanoate, melting point 49° C., $[\alpha]_D^{20}= -29.5$ (in dioxane). On replacing the decanoyl chloride in this procedure by heptanoyl chloride, the 3-heptanoate was obtained, oil with $[\alpha]^{20}= -33.5$ (in dioxane).

EXAMPLE VIII (a) 19-Acetylthiomethyl-Δ$^4$-androstene-3,17-dione 4.0 ml of acetic anhydride were added to a solution of 1.5 g of 19-(mercaptomethyl)-Δ$^4$-androstene-3,17-dione in 75 ml of pyridine under a nitrogen atmosphere. The mixture was stirred overnight at room temperature and was then poured out into ice water, while 40 ml of 2N hydrochloric acid were added simultaneously. Extraction with methylene chloride, evaporation of the extract and chromatography of the residue gave 1.4 g of 19-acetylthiomethyl-Δ$^4$-androstene-3,17-dione, melting point 106°–114° C., $[\alpha]_D^{20}= +135$ (in dioxane).

(b) Other 19-acetylthiomethYl compounds

Following a similar procedure to that described in Example VIII (a), with acetic anhydride replaced by propionic anhydride, butyryl chloride or cyclo-octylacetyl chloride, the following 19-acylthiomethyl compounds were obtained, respectively: 19-propionylthiomethyl-Δ$^4$-androstene-3,17-dione, 19-butyrylthiomethyl-Δ$^4$-androstene-3,17-dione and 19-cyclooctylacetylthiomethyl-Δ$^4$-androstene-3,17-dione.

EXAMPLE IX

17β-Hydroxy-19-methylthiomethyl-Δ$^4$-androsten-3-one 0.3 g of NaBH$_4$ was added at a temperature of −12° C. to a stirred solution of 5 g of 19-methylthiomethyl-Δ$^4$-androstene-3,17-dione in a mixture of 60 ml of tetrahydrofuran and 60 ml of methanol, under a nitrogen atmosphere. The mixture was stirred for 30 minutes at −12° C., then neutralised with acetic acid (50% strength) and poured out into ice water. The mixture was extracted with methylene chloride/tetrahydrofuran. The extract was evaporated and the residue was recrystallised from methylene chloride/ether. Yield: 3.5 g of 17β-hydroxy-19-methylthiomethyl-Δ$^4$-androsten-3-one.

Esterification with heptanoyl chloride in the conventional manner gave the 17β-heptanoate.

EXAMPLE X

19-Methyldithio-Δ$^4$-androstene-3,17-dione 0.26 g of sodium amide was added to a solution of 1.9 g of 19-mercapto-Δ$^4$-androstene-3,17-dione in 32 ml of tetrahydrofuran. After the mixture had been stirred for half an hour at room temperature, a solution of 0.75 ml of S-methylmethanethiosulphonate (obtained by oxidation of dimethyl disulphide with 30% strength hydrogen peroxide and purification by fractional distillation, boiling point 84°–85° C./2.5 mmHg pressure) in 5 ml of tetrahydrofuran was added dropwise. After the reaction mixture had been stirred for 1 hour at room temperature, it was diluted with methylene chloride and washed with a 5% strength NaHCO$_3$ solution and then with water until neutral.

After evaporation, the residue was purified by chromatography and crystallisation from methylene chloride/ether.

Yield: 1.3 g of 19-methyldithio-Δ$^4$-androstene-3,17-dione, melting point 144°–145° C., $[\alpha]_D^{20}= +248$ (in dioxane).

EXAMPLE XI

19-Methyldithio-Δ$^4$-androstene-3,17-dione 22.5 ml of a 1.0M solution of triethyloxonium tetrafluoborate in methylene chloride were added dropwise to a solution of 3 ml of dimethyl disulphide in 45 ml of methylene chloride at 0°–5° C. After this solution had been stirred for 1.5 hours at 0°–5° C., a solution of 4.8 g of 19-mercapto-Δ$^4$-androstene-3,17-dione and 3 ml of triethylamine in 45 ml of methylene chloride was added dropwise.

The reaction mixture was stirred for half an hour at 0°–5° C. and 3 hours at room temperature, and was then diluted with methylene chloride and washed with a 5% strength NaHCO$_3$ solution and then with water until neutral.

After evaporation, the residue was purified by chromatography and crystallisation from methylene chloride/ether.

Yield: 2.5 g of 19-methyldithio-Δ$^4$-androstene-3,17-dione, melting point 144°–145° C., $[\alpha]_D^{20}= +248$ (in dioxane).

EXAMPLE XII (a) 3β-Hydroxy-19-methyldithio-Δ$^5$-androsten-17-one

Following a similar procedure to that described in Example X, 2.5 g of 3β-hydroxy-19-mercapto-Δ$^5$-androsten-17-one were converted to 1.2 g of the title compound, melting point 119°–120° C., $[\alpha]_D^{20}= -88.4$ (in dioxane).

(b) 3-Esters

Following a similar procedure to that described in Example VII, 3β-hydroxy-19-methyldithio-Δ$^5$-androsten-17-one was converted to its 3-propionate (with propionic anhydride) and its 3-dodecanoate (with dodecanoyl chloride).

EXAMPLE XIII (a) 19-(t.Butyldithio)androst-4-ene-3,17-dione

In 100 ml dry ether 2.85 ml t.butanethiol were stirred for 1 hour with 5.75 g di-t.butyldiazocarboxylate in the presence of a catalytic amount sodium methoxide. The ether was evaporated and the solid adduct was crystallised from hexane. Yield: 7.5 g adduct, melting point 92°–98° C.

A solution of 16.g 19-mercapto-androst-4-ene-3,17-dione in 20 ml dimethylformamide (DMF) was added dropwise to a solution of 5 g of the above adduct in 100 ml DMF. The mixture was stirred for 4 hours at room temperature and then poured out in 500 ml of water. The product was extracted with $CH_2Cl_2$. The organic phase was evaporated and the residue was purified by chromatography ($SiO_2$; hexane (ethyl acetate 65/35) giving 1.7 g of the title compound, oil with $[\alpha]_D^{20} = +266$ (in dioxane).

(b) 19-Pentyldithio-androst-4-ene-3,17-dione

The title compound was prepared in a similar way as described in Example XIII (a), using pentanethiol instead of t.butanethiol. Oil with $[\alpha]_D^{20} = +219$ (in dioxane).

(c) 19-Decyldithio-androst-4-ene-3,17-dione

The title compound was prepared in a similar way as described in Example XIII (a), using decanethiol instead of t.butanethiol. Oil with $[\alpha]_D^{20} = +174$ (in dioxane).

EXAMPLE XIV (a) 19-Methoxycarbonyldithio-androst-4-ene-3,17-dione

Methoxycarbonylsulphenylchloride (1.95 ml) was added dropwise to a solution of 6.2 g of 19-mercapto-androst-4-ene-3,17-dione in 200 ml methanol at 0° C. After stirring for 15 minutes the mixture was poured out in 1 liter $NaHCO_3$ (1%) solution. Extraction with $CH_2Cl_2$ and evaporation of the organic phase gave an oil, that was purified by chromatography ($SiO_2$; $CH_2Cl_2$/acetone 95/5) yielding 4.5 g of the title compound, $[\alpha]_D^{20} = +180°$ (in dioxane).

(b) 19-Isopropyldithio-androst-4-ene-3,17-dione

To a solution of 0.8 g of the product of Example XIV (a) in 16 ml methanol 0.2 ml isopropanethiol was added, followed by 1 drop triethylamine. After stirring for 1 hour the reaction mixture was poured out in 150 ml of water. Extraction with $CH_2Cl_2$ and evaporation of the organic phase gave a residue that was chromatographed on $SiO_2$ with hexane/ethylacetate 65/35. Yield: 0.6 g of the title compound, melting point 125°–126° C., $[\alpha]_D^{20} = +246$ (in dioxane).

(c) Other 19-($R_4$-S-S-)androst-4-ene-3,17-diones

In a similar way as described in Example XIV (b) using the appropriate thiol the following compounds were prepared:
19-Ethyldithio-androst-4ene-3,17-dione, $R_f = 0.45$; $CH_2Cl_2$/acetone 95/5;
19-(2,3-dihydroxypropyldithio)-androst-4-ene-3,17-dione, $[\alpha]_D^{20} = +215$ (in dioxane);
19-(2-hydroxyethyldithio)-androst-4-ene-3,17-dione, $[\alpha]_D^{20} = +234$ (in dioxane);
19-(octyldithio)-androst-4-ene-3,17-dione, $[\alpha]_D^{20} = +205$ (in dioxane);
19-(carboxymethyldithio)-androst-4-ene-3,17-dione, $R_f = 0.30$; $Ch_2Cl_2$/methanol 85/15.

EXAMPLE XV 19-(2-Carboxy-2-amino ethyldithio)-androst-4-ene-3,17-dione

19-Mercapto-androst-4-ene-3,17-dione (159 mg) and 300 mg Boc-cys(SCM)-OH.dicyclohexylamine salt (Boc=t.butyloxycarbonyl; SCM=methoxycarbonyl-sulphenyl) were dissolved in 3 ml methanol and the solution was stirred under nitrogen for 2 hours at room temperature. The solvent was then evaporated and the residue was dissolved in 20 ml of $CH_2Cl_2$. The organic phase was washed with 0.5N HCl and water and then dried and evaporated. The residue was purified by chromatography on $SiO_2$ (toluene/ethanol/ethyl acetate/acetic acid 5/1/5/0.1, yielding 223 mg 19-(2-carboxy-2-Boc-amino-ethyldithio)-androst-4-ene-3,17-dione, melting point 76°–80° C.

This compound was dissolved in a mixture of 2 ml trifluoro-acetic acid, 0.2 ml water and 0.2 ml anisole. After stirring for 1 hour at room temperature the solution was evaporated and the residue was dissolved in 10 ml t.butanol/$H_2O$ (1/1). This solution was treated with Dowex-OAc and then lyophilised. The residue was dissolved in 10 ml t.butanol/$H_2$ (1) and 1 equivalent 1N HCl was added. The solution was lyophilised again, yielding 120 mg of the HCl-salt of the title compound, melting point 138°–140° C.

EXAMPLE XVI (a) 3-Hydroxy-19-(isopropyldithio)androst-5-en-17-one

In a similar way as described in Example XIV, starting from 19-mercapto-3-hydroxy-androst-5-en-17-one, the title compound was obtained, melting point 168°–169° C., $[\alpha]_D^{20} = -98$ (in dioxane).

(b) 3-Hydroxy-19-(2-hydroxyethyldithio)-androst-5-en-17-one

In a similar way as described in Example XVI (a) and using 2-mercaptoethanol instead of isopropanethiol, the title compound was obtained, melting point 129°–130° C. $[\alpha]_D^{20} = -80$ (in dioxane).

EXAMPLE XVII (a) 3β-Hydroxy-19-t.butyldithio-androst-5-en-17-one

In a similar way as described in Example XIII, starting from 19-mercapto-3β-hydroxy-androst-5-en-17-one and using t.butanethiol the title compound was obtained, melting point 188°–190° C.; $[\alpha]_D^{20} = -106.8$ (in dioxane).

(b) Other 3β-hydroxy-19-$R_4$SS-androst-5-en-17-ones

Similarly, the following compounds were prepared: 3β-hydroxy-19-pentyldithio-androst-5-en-17-one, melting point 81°–82° C., $[\alpha]_D^{20} = -87$ (in dioxane); 3β-hydroxy-19-decyldithio-androst-5-en-17-one, melting point 68°–70° C., $[\alpha]_D^{20} = -73$ (in dioxane).

EXAMPLE XVIII (a)

3β-Hydroxy-19-acetylthiomethyl-Δ⁵-androsten-17-one

Potassium thioacetate (7 g) was added to a solution of 7 g 3β-hydroxy-19-tosyloxymethyl-Δ⁵-androsten-17-one in 140 ml of dimethylformamide, after which the stirred solution was heated to 100° C. under a nitrogen atmosphere for 1 hour and 15 minutes. After having cooled to room temperature and been poured out into ice water, the reaction mixture was extracted with a mixture of methylene dichloride and tetrahydrofuran. After evaporating the extract, the residue was purified by chromatography on $SiO_2$.

Yield: 2.4 g of the title compound.

(b)

3β-Hydroxy-19-mercaptomethyl-Δ⁵-androsten-17-one 513 mg of sodium methoxide were added to a stirred solution of 1.77 g of 3β-hydroxy-19-acetylthiom ethyl-Δ⁵-androsten-17-one in 90 ml of methanol under a nitrogen atmosphere. After having been stirred for 3 hours at room temperature, the reaction mixture was neutralised with 50% strength acetic acid and poured out into ice water. Extraction with methylene dichloride/tetrahydrofuran, evaporation of the extract, chromatography of the residue over silica gel and recrystallisation from methylene dichloride/diethyl ether gave 0.53 g of the title compond.

(c) 19-Mercaptomethyl-Δ⁴-androstene-3,17-dione 1.5 ml of cyclohexanone and a solution of 0.3 g of aluminium isopropoxide in 1 ml of dry toluene were added to a solution of 0.25 g of 3β-hydroxy-19-mercaptomethyl-Δ⁵-androsten-17-one in 10 ml of dry toluene. The mixture was boiled for 45 minutes under a nitrogen atmosphere. After addition of 1.6 g of sodium potassium tartrate, the reaction mixture was poured out into water and extracted with methylene dichloride. After evaporation of the extract, the residue was purified by chromatography over silica gel, yielding 0.24 g of the title compound.

(d)

3β-Hydroxy-19-acetylthiomethyl-Δ⁵-androsten-17-one 3-undecanoate

In a similar way as described in Example VII using undecanoylchloride the title ester was prepared.

(e) 19-Acetylthiomethyl-Δ⁴-androstene-3,17-dione and the corresponding Δ⁵ compound.

Oxidation of the product of Example XVIII (a) with pyridinium chlorochromate (cf. Example III) gave a mixture of the Δ⁴ and Δ⁵ title compounds. Separation by chromatography gave the title compounds.

EXAMPLE XIX

19-Methylthiomethyl-Δ⁴-androstene-3β, 17β-diol and the corresponding 3α-ol

Repeating the procedure of Example IX with an excess of $NaBH_4$ gave a mixture of the title compounds, that was separated by chromatography.

We claim:

1. Novel Δ⁴- and Δ⁵-androstene derivatives having the formula:

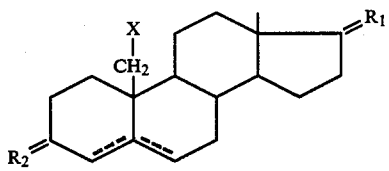

wherein
X=S—S—R₄;
R₁=O or H (βR₅);
R₂=O or H (βR₆):
R₄=acyl (1–18 C) or alkyl (1–18 C), which is unsubstituted or substituted by hydroxy, oxo, alkoxy, mercapto, alkylthio, amino, substituted amino, carboxyl and/or ester groups;
R₅=OH, O-acyl (1–18 C) or an ether group;
R₆=OH, O-acyl (1–18 C) or an ether group; and the dotted lines represent a carbon-carbon bond in 4,5- or 5,6-position.

2. Compounds according to claim 1, wherein R₁=O.
3. Compounds according to claim 1, wherein R₂=O, H (βOH) or H/βO acyl(1–18C).
4. A pharmaceutical composition having aromatase-inhibiting properties comprising an aromatase-inhibiting effective amount of a compound of claim 1 and a pharamaceutically acceptable carrier.
5. A compound according to claim 2, wherein R₂ is O, H(βOH), or H/βO acyl(1–18C).
6. A pharmaceutical composition having aromatase-inhibiting properties comprising an aromatase-inhibiting effective amount of a compound of claim 2 and a pharmaceutically acceptable carrier.
7. A pharmaceutical composition having aromatase-inhibiting properties comprising an aromatase-inhibiting effective amount of a compound of claim 3 and a pharmaceutically acceptable carrier.
8. A pharmaceutical composition having aromatase-inhibiting properties comprising an armoatase-inhibiting effective amount of a compound of claim 5 and a pharmaceutically acceptable carrier.

* * * * *